US011801327B2

(12) United States Patent
Kang et al.

(10) Patent No.: US 11,801,327 B2
(45) Date of Patent: Oct. 31, 2023

(54) INTEGRATED ORGAN AND TISSUE PRINTING METHODS, SYSTEM AND APPARATUS

(71) Applicant: Wake Forest University Health Sciences, Winston-Salem, NC (US)

(72) Inventors: Hyun-Wook Kang, Winston-Salem, NC (US); Sang Jin Lee, Winston-Salem, NC (US); Anthony Atala, Winston-Salem, NC (US); James J. Yoo, Winston-Salem, NC (US)

(73) Assignee: WAKE FOREST UNIVERSITY HEALTH SCIENCES, Winston-Salem, NC (US)

( * ) Notice: Subject to any disclaimer, the term of this patent is extended or adjusted under 35 U.S.C. 154(b) by 258 days.

(21) Appl. No.: 17/237,116

(22) Filed: Apr. 22, 2021

(65) Prior Publication Data
US 2021/0252188 A1    Aug. 19, 2021

Related U.S. Application Data

(60) Division of application No. 15/672,885, filed on Aug. 9, 2017, now Pat. No. 11,013,825, which is a division
(Continued)

(51) Int. Cl.
*A61L 27/20* (2006.01)
*A61L 27/22* (2006.01)
(Continued)

(52) U.S. Cl.
CPC .............. *A61L 27/20* (2013.01); *A61L 27/222* (2013.01); *A61L 27/225* (2013.01); *A61L 27/26* (2013.01);
(Continued)

(58) Field of Classification Search
CPC ...... A61L 27/20; A61L 27/222; A61L 27/225; A61L 27/26; A61L 27/38; A61L 27/52;
(Continued)

(56) References Cited

U.S. PATENT DOCUMENTS 5,490,962 A    2/1996  Cima et al.
5,518,680 A    5/1996  Cima et al.
(Continued)

FOREIGN PATENT DOCUMENTS

WO    2010030964 A2    3/2010
WO    2010042856 A2    4/2010

OTHER PUBLICATIONS

Ciocca L and Scotti R. CAD-CAM generated ear case by means of a laser scanner and rapid prototyping machine. The Journal of Prosthetic Dentistry. Dec. 2004;92: 591-595.
(Continued)

*Primary Examiner* — Anh T Vo
(74) *Attorney, Agent, or Firm* — Myers Bigel, P.A.

(57) ABSTRACT

A method of making an organ or tissue comprises: (a) providing a first dispenser containing a structural support polymer and a second dispenser containing a live cell-containing composition; (b) depositing a layer on said support from said first and second dispenser, said layer comprising a structural support polymer and said cell-containing composition; and then (c) iteratively repeating said depositing step a plurality of times to form a plurality of layers one on another, with separate and discrete regions in each of said layers comprising one or the other of said support polymer or said cell-containing composition, to thereby produce provide a composite three dimensional structure containing both structural support regions and
(Continued)

High strength tissue engineered constructs can be fabricated by an integrated organ printing system.

cell-containing regions. Apparatus for carrying out the method and composite products produced by the method are also described.

10 Claims, 6 Drawing Sheets

Related U.S. Application Data of application No. 14/476,359, filed on Sep. 3, 2014, now Pat. No. 9,764,516, which is a continuation of application No. 13/267,448, filed on Oct. 6, 2011, now abandoned.

(60) Provisional application No. 61/390,342, filed on Oct. 6, 2010.

(51) Int. Cl.

| | | |
|---|---|---|
| *A61L 27/26* | (2006.01) | |
| *A61L 27/38* | (2006.01) | |
| *A61L 27/52* | (2006.01) | |
| *B29C 64/112* | (2017.01) | |
| *B29C 64/124* | (2017.01) | |
| *B29C 64/393* | (2017.01) | |
| *B33Y 70/00* | (2020.01) | |
| *C12M 3/00* | (2006.01) | |
| *C12M 1/00* | (2006.01) | |
| *C12M 1/26* | (2006.01) | |
| *A61K 35/12* | (2015.01) | |
| *B33Y 10/00* | (2015.01) | |
| *B33Y 30/00* | (2015.01) | |
| *B33Y 80/00* | (2015.01) | |
| *B29K 105/00* | (2006.01) | |
| *B29K 267/00* | (2006.01) | |
| *B29L 31/00* | (2006.01) | |

(52) U.S. Cl.
CPC ............ *A61L 27/38* (2013.01); *A61L 27/52* (2013.01); *B29C 64/112* (2017.08); *B29C 64/124* (2017.08); *B29C 64/393* (2017.08); *B33Y 70/00* (2014.12); *A61K 35/12* (2013.01); *B29K 2105/0005* (2013.01); *B29K 2267/04* (2013.01); *B29L 2031/7532* (2013.01); *B33Y 10/00* (2014.12); *B33Y 30/00* (2014.12); *B33Y 80/00* (2014.12); *C12M 21/08* (2013.01); *C12M 23/50* (2013.01); *C12M 33/00* (2013.01)

(58) Field of Classification Search
CPC ..... A61K 35/12; B29C 64/112; B29C 64/124; B29C 64/393; B29K 2105/0005; B29K 2267/04; B29L 2031/7532; B33Y 10/00; B33Y 30/00; B33Y 70/00; B33Y 80/00; C12M 21/08; C12M 23/50; C12M 33/00; C08L 5/08

See application file for complete search history.

(56) References Cited

U.S. PATENT DOCUMENTS

| | | |
|---|---|---|
| 6,176,874 B1 | 1/2001 | Vacanti et al. |
| 6,455,311 B1 | 9/2002 | Vacanti |
| 6,548,263 B1* | 4/2003 | Kapur .................. C12M 25/06 216/2 |
| 6,804,579 B1 | 10/2004 | Laski |
| 6,986,739 B2 | 1/2006 | Warren et al. |
| 7,051,654 B2 | 5/2006 | Boland et al. |
| 7,531,503 B2 | 5/2009 | Atala et al. |
| 8,143,055 B2* | 3/2012 | Forgacs ............. A61L 27/3625 435/395 |
| 8,747,880 B2* | 6/2014 | Forgacs ............. A61L 27/3886 623/23.72 |
| 9,764,515 B2 | 9/2017 | Yost et al. |
| 2003/0049839 A1* | 3/2003 | Romero-Ortega ... C12N 5/0622 435/303.1 |
| 2003/0096406 A1 | 5/2003 | Atala et al. |
| 2003/0175410 A1 | 9/2003 | Campbell et al. |
| 2004/0253365 A1* | 12/2004 | Warren ................ B05C 5/0216 118/715 |
| 2006/0094112 A1 | 5/2006 | Babalola et al. |
| 2009/0117087 A1 | 5/2009 | Carroll et al. |
| 2009/0208466 A1 | 8/2009 | Yoo et al. |
| 2009/0208577 A1 | 8/2009 | Xu et al. |
| 2009/0275129 A1 | 11/2009 | Cooper et al. |
| 2010/0041134 A1* | 2/2010 | Forgacs ................ C12M 25/06 435/325 |
| 2010/0160183 A1 | 6/2010 | Xu et al. |
| 2010/0185174 A1 | 7/2010 | Boyden et al. |
| 2011/0172611 A1 | 7/2011 | Yoo et al. |
| 2011/0212501 A1 | 9/2011 | Yoo |

OTHER PUBLICATIONS

Golden et al., Lab Chip 7, pp. 720-725 (2007).
Leukers et al., Journal of Material Science: Materials in Medicine 16 (2005) pp. 1121-1124.
Li B et al. A robust true direct-print technology for tissue engineering. Proceedings of the 2007 International Manufacturing Science and Engineering Conference. Oct. 15-17, 2007; 1-6.
Mironov V et al. Organ printing: computer-aided jet-based 3D tissue engineering. Trends in Biotechnology. Apr. 2003; 21(4): 157-161.
Nakamura M et al. Biocompatible inkjet printing technique for designed seeding of individual living cells. Tissue Engineering. 2005; 11(11/12); 1658-1666.

\* cited by examiner

Figure 1. High strength tissue engineered constructs can be fabricated by an integrated organ printing system.

Figure 2. Schematic diagram of integrated organ printing system

Figure 3. Visualized 3D pattern to construct a hybrid structure

Figure 4. Fabricated a line with (a) gelatin 20 mg/ml, fibrinogen 10 mg/ml, glycerol 10%v/v and Hyaluronic acid 3 mg/ml and (b) gelatin 10 mg/ml, fibrinogen 10 mg/ml, glycerol 10%v/v and hyaluronic acid 6 mg/ml.

Figure 5. Fabricated branch pattern with cells labeled with fluorescence dyes

Figure 6. SEM images of fabricated high strength tissue engineered construct

Figure 7. Expected cross section of the fabricated hybrid structure (a) and fluorescence image (b)

Figure 8. Microscope and fluorescence images of live/dead staining result on day 1 and day 5.

Figure 9. Cell viability (left) and proliferation test (right) results of the tissue engineered construct

INTEGRATED ORGAN AND TISSUE PRINTING METHODS, SYSTEM AND APPARATUS

RELATED APPLICATIONS

The present application is a divisional of U.S. patent application Ser. No. 15/672,885, filed Aug. 9, 2017, now allowed, which is a divisional of U.S. patent application Ser. No. 14/476,359, filed Sep. 3, 2014, which is a continuation of U.S. patent application Ser. No. 13/267,448, filed Oct. 6, 2011, which claims the benefit of U.S. Provisional Application No. 61/390,342, filed Oct. 6, 2010, the disclosures of each of which are incorporated by reference herein in their entireties.

STATEMENT OF FEDERAL SUPPORT

This invention was made with government support under Grant Number W81XWH-07-1-0718 awarded by the Telemedicine & Advanced Technology Research Center (TATRC) of the Department of Defense. The government has certain rights in the invention.

FIELD OF THE INVENTION

The present invention concerns methods, systems, and apparatus for making tissues in vitro for subsequent implantation in vivo.

BACKGROUND OF THE INVENTION

Conventional organ printing technology (ink-jet printing) makes it possible to place viable cells in a three dimensional architecture. See, e.g., U.S. Pat. No. 7,051,654. And, various cells can be concurrently printed in an accurate manner. Because a tissue/organ has a complex structure, the organ printing technology is the most promising potential technology to mimic the anatomical structure of tissues or organs.

However, with ink-jet cell printing techniques, the material being processed must be a low viscosity gel. As a result, high aspect ratio structures, or porous structures that facilitate the transport of nutrient and oxygen into the construct, cannot easily be achieved. This is because the low viscosity materials being printed have relatively low mechanical stability. In addition, the printing materials are easily deformed in liquid by swelling or shrinkage. Hence, after implantation of tissue engineered scaffolds made by organ printing, it is difficult to preserve the pre-defined shape of the structure and protect immature cells or tissue therein.

The production of living organs and tissues by injection molding of forms generated by CAD/CAM has been described, but such methods again make the preservation of pre-defined shapes difficult. See, e.g., U.S. Pat. No. 6,773,713.

Accordingly, there is a need for new techniques for generating tissues, tissue scaffolds, and organs containing live cells for implantation.

SUMMARY OF THE INVENTION

A first aspect of the invention is an integrated organ and/or tissue printing system, comprising:
(a) a support stage for supporting an organ to be printed thereon;
(b) a positioning unit (as a single component or separate components) above, below, or adjacent the support stage and operatively associated therewith;
(c) a plurality, or at least a pair (e.g., two, or more) of dispensers or syringes connected to the positioning unit, each of the dispensers or syringes comprising a nozzle,
(d) a syringe activator operatively associated with each of the pair of syringes for independently and selectively dispensing the contents thereof;
(d) a temperature regulator operatively associated with at least one (or both, or all) of the syringes for independently regulating the temperature of at least one (or both) of the pair of syringes; and
(e) a positioning controller operatively associated with the positioning unit, the support stage, or both the positioning unit and the support stage, for adjusting in three dimensions the position of the support stage in relation to the at least a pair of syringes during printing of an organ or tissue on the support stage.

In some embodiments, the temperature regulator comprises a thermal element (e.g., heater, a cooler, or a heat exchanger, such as liquid chiller systems, resistive heaters, thermoelectric devices or Peltier coolers, etc.) operatively associated with the syringe (e.g., the syringe reservoir, the syringe nozzle, or both, separately or concurrently, to regulate the storage temperature and deposition temperature of the material being dispensed).

In some embodiments, the temperature regulator further comprises: a temperature sensor operatively associated with the syringe (e.g., the reservoir, the nozzle, or both); and a temperature controller operatively associated with the temperature sensor and the thermal element for independently controlling the temperature of at least one (or both) of the pair of syringes.

In some embodiments, a first member of the pair of syringes has a heater operatively associated with the syringe reservoir (e.g., for heating a synthetic polymer in the reservoir).

In some embodiments, a second member of the pair of syringes has a cooler or heat exchanger operatively associated with the syringe reservoir (e.g., for cooling live cells contained in the reservoir).

In some embodiments, the positioning unit comprises a 3-axis stage system.

In some embodiments, the apparatus further comprises a CAD/CAM system operatively associated with the positioning controller and configured for adjusting in three dimensions in a predetermined pattern the position of the support stage in relation to the at least a pair of syringes during printing of an organ or tissue (e.g., a composite tissue) in a plurality of layers on the support stage.

In some embodiments, the CAD/CAM system is operatively associated with the syringe activators and configured to selectively deposit the contents of each of the syringes in independent locations in a predetermined pattern in each of the layers.

In some embodiments, the dispensers or syringes are activated, independently, by pneumatic pressure, hydraulic pressure, mechanical pressure or pumping.

In some embodiments, the nozzles of the dispensers syringes have an inner diameter of from 5, 10 or 50 um, up to 500, 800 or 1000 um, or more.

In some embodiments, each of the dispensers or syringes further comprises a reservoir, with the reservoir optionally (but in some embodiments preferably) mounted on the positioning unit.

A further aspect of the invention is a method of printing an organ or tissue in a plurality of layers, comprising:
  (a) providing a first dispenser (e.g., a syringe) containing a structural support polymer and a second dispenser (e.g., a syringe) containing a live cell-containing composition (e.g., by providing an apparatus as described herein);
  (b) depositing a layer on said support from said first and second dispenser, said layer comprising a structural support polymer and said cell-containing composition (e.g., a hydrogel); and then
  (c) iteratively repeating said depositing step a plurality of times to form a plurality of layers one on another, with separate and discrete regions in each of said layers separately deposited by one or the other of said syringes or separately comprising one or the other of said structural support polymer and said cell containing composition, to thereby produce provide a composite three dimensional structure containing both structural support regions and cell-containing regions. The iteratively repeating step may be carried out from 5, 10, 50 or 100 times up to 3000 or 5000 times, or more. Each of the layers deposited during each step is typically from 5, 10 or 20 um thick up to 500, 800 or 1000 um thick.

In some embodiments, the structural support polymer is deposited in a plurality of regions in a plurality of adjacent layers at least partially overlapping one another to form a supporting matrix interconnecting the plurality of adjacent layers.

In some embodiments, the cell support composition comprises live cells (for example, for example, stem cells, progenitor cells and differentiated cells; cartilage cells, mesenchymal stem cells, bone cells, muscle cells, skin cells, pancreatic cells, kidney cells, nerve cells, liver cells, etc.).

In some embodiments, the method further comprises chilling the dispenser or syringe containing the cell support composition, and/or heating the dispenser or syringe containing the structural support polymer.

In some embodiments, the structural support polymer is stable (e.g., to provide support for at least some fixed period of time after implantation); in other embodiments, the structural support polymer is sacrificial (e.g., water soluble, to provide support during manufacture).

In some embodiments, the apparatus comprising a third syringe containing a sacrificial polymer different from the structural support polymer, and with the sacrificial polymer deposited in a plurality of regions in a plurality of adjacent layers at least partially overlapping one another, to form a sacrificial network interconnecting a plurality of adjacent layers.

In some embodiments, the method further comprises the step of removing the sacrificial polymer (e.g., by washing or rinsing with an aqueous solution).

In some embodiments, the apparatus further comprises an additional dispenser or syringe, optionally chilled, for depositing a second cell support composition different from the first cell support composition (and optionally containing a second cell type different from the first cell type); the method further comprising: depositing the second cell support compositions in the structure in regions separate and discrete from the first cell support composition (e.g., to thereby form a tissue composite);

In some embodiments, the structural support polymer is dispensed from its corresponding nozzle at a temperature of at least about 25, 27, 30, 32, 35, 40, or 50 degrees Celsius (up to 80 or 100 degrees Celsius or more).

In some embodiments, the cell support composition(s) is/are dispensed from its corresponding nozzle at a temperature of not more than about 30, 27, 25, 23, 20, 17, 15 or 10 degrees Celsius (down to 5, 0, or −10 degrees Celsius, or less).

In some embodiments, the cell support composition(s) is/are dispensed from its/their corresponding nozzle at a temperature at least 3, 5, 7, 10, 12, 15, or 20 degrees Celsius less than the temperature at which the structural support polymer is dispensed through its/their corresponding nozzle(s).

A further aspect of the invention is a three dimensional tissue or organ construct comprising a solid support (e.g., in the form of a three dimensional, optionally porous, matrix) and a live cell-containing composition in separate and discrete regions therein, the construct optionally but preferably produced by the methods described herein. In some embodiments the construct may further contain pores, cavities, chambers, vessel lumens or channels formed therein, separately or interconnected with one another (e.g., by removal of sacrificial polymer regions). In some embodiments the construct may comprises a tissue composite (e.g., comprises two or more of skin/epithelium, bone, cartilage, skeletal muscle, tendon, and/or ligament tissue, etc; and/or two or more of endothelium and smooth muscle tissue). In some embodiments the composite comprises 2 or more different tissues, the two or more different tissues sharing a common, integrally formed and connected, solid support scaffold.

The foregoing and other objects and aspects of the present invention are explained in further detail in the drawings herein and the specification set forth below. The disclosures of all United States Patent references cited herein are incorporated by reference herein in their entirety.

DETAILED DESCRIPTION OF EMBODIMENTS OF THE INVENTION

This invention concerns, among other things, high strength engineered construct including various viable cells made by integrating certain aspects of ink-jet printing technology (for example, as described in Yoo et al., US Patent Application Publication No. 2009/0208466) with certain aspects of solid freeform fabrication (SFF) technology. Therefore, the fabricated constructs are composed of two or more parts: a cell-contained gel or hydrogel structure, a solidified polymer or structural polymer scaffold, and optionally a network of pores, channels or other openings formed by deposition and subsequent removal of a sacrificial polymer therein. The polymer scaffold provides such a frame to protect the cell-contained gel structure from the external load. This integrated organ printing system provides highly flexible design capability for making three-dimensional engineered constructs which contain various cells with accurate localization thereof.

In some embodiments, the integrated organ printing system comprises a multi-nozzle dispensing system, temperature controller module, and 3-axis stage system. Multi-nozzle dispensing system is for precise dispensing of polymer materials and cell-contained gel materials in a single construct. The dispensing system is composed of precise pressure controller, multi-syringes and multi-nozzles having micro-scale inner diameter. The temperature controller is to prepare dispensable fluid for thermoplastic material by heating up to melting temperature. 3-axis stage system is for printing designed 3D patterns using the precisely dispensed materials.

Cells and Cell Compositions.

Although not required, cells can typically be printed in the form of a "cell composition" that comprises a liquid (e.g., a gel or viscous gel) carrier for the cells. The cell composition can be in the form of a suspension, solution, or any suitable form. Examples of suitable carriers include, but are not limited to, water, ionic buffer solutions (e.g., phosphate buffer solution, citrate buffer solution, etc.), liquid (including gel) media (e.g., modified Eagle's medium ("MEM"), Hanks' Balanced Salts, etc.), and so forth. For instance, the use of a liquid (including gel) carrier in the cell composition can ensure adequate hydration and minimize evaporation of the cells after printing.

In one embodiment, the carrier composition is a hydrogel. In one embodiment, the carrier composition is a stable hydrogel (e.g., a cross-linked hydrogel, crosslinked before or after deposition) that is stable after deposition under conditions such as elevated temperature in which a sacrificial polymer or hydrogel is removed, as discussed further below.

Any type of cell may be printed using the methods herein, including prokaryotic and eukaryotic cells. Examples of eukaryotic cells that may be printed using the methods herein include, but are not limited to, mammalian cells (e.g., dog, cat, primate, human), including stem cells (e.g., embryonic and amniotic fluid), progenitor cells and differentiated cells, without limitation. Particular examples include but are not limited to stem cells, progenitor cells and differentiated cells; cartilage cells, mesenchymal stem cells, bone cells, muscle cells, skin cells, pancreatic cells, kidney cells, nerve cells, liver cells, etc, and the various cell types discussed below.

Stem cells have the ability to replicate through numerous population doublings (e.g., at least 60-80), in some cases essentially indefinitely, and also have the ability to differentiate into multiple cell types (e.g., is pluripotent or multipotent). It is also possible for cells to be transfected with a compound of interest that results in the cells becoming immortalized (i.e., able to double more than 50 times). For example, it has been reported that mammalian cell transfection with telomerase reverse transcriptase (hTERT) can immortalize neural progenitor cells (See U.S. Pat. No. 7,150,989 to Goldman et al.).

"Embryonic stem cell" as used herein refers to a cell that is derived from the inner cell mass of a blastocyst and that is pluripotent.

"Amniotic fluid stem cell" as used herein refers to a cell, or progeny of a cell, that (a) is found in, or is collected from, mammalian amniotic fluid, mammalian chorionic villus, and/or mammalian placental tissue, or any other suitable tissue or fluid from a mammalian donor, (b) is pluripotent; (c) has substantial proliferative potential, (d) optionally, but preferably, does not require feeder cell layers to grow in vitro, and/or (e) optionally, but preferably, specifically binds c-kit antibodies (particularly at the time of collection, as the ability of the cells to bind c-kit antibodies may be lost over time as the cells are grown in vitro).

"Pluripotent" as used herein refers to a cell that has complete differentiation versatility, e.g., the capacity to grow into any of the animal's cell types. A pluripotent cell can be self-renewing, and can remain dormant or quiescent with a tissue. Unlike a totipotent cell (e.g., a fertilized, diploid egg cell) a pluripotent cell cannot usually form a new blastocyst.

"Multipotent" as used herein refers to a cell that has the capacity to grow into any of a subset of the corresponding animal cell types. Unlike a pluripotent cell, a multipotent cell does not have the capacity to form all of the cell types of the corresponding animal.

"Cartilage cells" include those cells normally found in cartilage, which cells include chondrocytes. "Chondrocytes" produce and maintain the extracellular matrix of cartilage, by, e.g., producing collagen and proteoglycans. Cartilage is a highly specialized connective tissue found throughout the body, and its primary function is to provide structural support for surrounding tissues (e.g., in the ear and nose) or to cushion (e.g., in the trachea and articular oints). Types of cartilage include hyaline cartilage (articular joints, nose, trachea, intervertebral disks (NP), vertebral end plates), elastic cartilage (tendon insertion site, ligament insertion site, meniscus, intervertebral disks (AP)), costochondral cartilage (rib, growth plate), and fibrocartilage (ear). The loss of cartilage in a subject can be problematic, as it has a very limited repair capacity.

"Mesenchymal stem cells" or "MSCs" are progenitors of chondrocytes. MSCs can also differentiate into osteoblasts. Cartilage cells/tissues produced by the processes described herein are useful for, among other things, implantation into a subject to treat cartilage injury or disease.

"Bone cells" include those cells normally found in bone, and include osteoblasts, osteoclasts, osteocytes, and any combination thereof. Bone cells/tissues produced by the processes described herein are useful for, among other things, implantation into a subject to treat bone fractures or defects, and/or promote bone healing.

"Muscle cells" include those cells normally found in muscle tissue, including smooth muscle cells, cardiac muscle cells, skeletal muscle cells, and any combination thereof. Muscle cells/tissues produced by the processes described herein are useful for, among other things, implantation into a subject to treat muscle injuries or defects, and/or promote muscle healing.

"Skin cells" include those cells normally found in skin, and include epidermal cells (e.g., keratinocytes, melanocytes, Merkel cells, Langerhan cells, etc., and any combination thereof) and dermal cells (e.g., fibroblasts, adipocytes, mast cells, macrophages, and any combination thereof). Skin tissue produced by the process of the present invention is useful for implantation into or on a subject to, for example, treat burns, and other wounds such as incisions, lacerations, and crush injuries (e.g., postsurgical wounds, and posttraumatic wounds, venous leg ulcers, diabetic foot ulcers, etc.)

"Pancreatic cells" include those cells normally found in the pancreas, and include pancreatic islet cells, e.g., glucagon-synthesizing A (.alpha.) cells, insulin-producing B (.beta.) cells, D (.delta.) cells, etc., and any combination thereof. Pancreatic islet tissue produced by the processes described herein is useful for, among other things, implantation into a subject to treat diabetes (including type I and type II diabetes).

"Kidney cells" include those cells normally found in the kidney, and include interstitial cells (e.g., interstitial peritubular cells which secrete erythropoietin), endothelial cells, etc., or any combination thereof.

"Nerve cells" include those cells normally found in the central and/or peripheral nervous system, including neuronal cells (e.g., cortical neurons, hippocampal neurons, dopaminergic neurons, cholinergic neurons, adrenergic neurons, noradrenergic neurons, etc., including any combination thereof), and glial cells (e.g., neuroglia, astrocytes, oligodendrocytes, Schwann cells, etc., including any combination thereof). Nerve cells produced by the processes described herein is useful, among other things, for implantation into a subject to treat nerve injury or degenerative diseases such as Parkinson's disease and Alzheimer's disease.

"Liver cells" include those cells normally found in the liver, and include hepatoblasts, hepatocytes, hepatic stellate cells, Kupffer cells, sinusoidal endothelial cells, etc., including any combination thereof. Livers cells produced by the processes described herein is useful, among other things, for implantation into a subject to treat acute or chronic liver disease.

Cells may be syngeneic (i.e., genetically identical or closely related, so as to minimize tissue transplant rejection), allogeneic (i.e., from a non-genetically identical member of the same species) or xenogeneic (i.e., from a member of a different species). Syngeneic cells include those that are autogeneic (i.e., from the subject to be treated) and isogeneic (i.e., a genetically identical but different subject, e.g., from an identical twin). Cells may be obtained from, e.g., a donor (either living or cadaveric) or derived from an established cell strain or cell line. For example, cells may be harvested from a donor (e.g., a potential recipient of a bioscaffold graft) using standard biopsy techniques known in the art.

According to some embodiments, at least a portion of the cells are viable after they are printed. "Viable cells" includes cells that adhere to a culture dish or other substrate and/or are capable of survival (e.g., proliferation). In some embodiments, at least 30, 40 or 50% of the total cells loaded are viable, and in further embodiments at least 60, 70, 80, or 90% or more of the total cells loaded are viable after printing. Cell viability may be measured by any conventional means, e.g., the MTS assay, and at a reasonable time after printing, e.g., 1 day after printing completion. Viability is measured upon incubation under conditions known in the art to be optimal for survival of the certain cells types present. For example, many eukaryotic cell types are typically incubated in a suitable medium at 5% carbon dioxide (95% atmospheric air) and 37 degrees Celsius.

Various mechanisms may be employed to facilitate the survival of the cells during and/or after printing. Specifically, compounds may be utilized that support the printed cells by providing hydration, nutrients, and/or structural support. These compounds may be applied to the substrate using conventional techniques, such as manually, in a wash or bath, through vapor deposition (e.g., physical or chemical vapor deposition), etc. These compounds may also be combined with the cells and/or compositions before and/or during printing, or may be printed or otherwise applied to the substrate (e.g., coated) as a separate layer beneath, above, and/or between cell layers. For example, one such support compound is a gel having a viscosity that is low enough under the printing conditions to pass through the nozzle of the print head, and that can gel to a stable shape during and/or after printing. Such viscosities are typically within the range of from about 0.5 to about 50 centipoise, in some embodiments from about 1 to about 20 centipoise, and in some embodiments, from about 1 to about 10 centipoise. Some examples of suitable gels that may be used in the present invention include, but are not limited to, agars, collagen, hydrogels, etc.

Another polymer used for hydrogels is alginate, a natural polysaccharide extracted from seaweed. One feature of alginate solutions is their gelling properties in the presence of divalent cations (e.g., $Mg^{++}$, $Ca^{++}$, $Sr^{++}$, $Ba^{++}$).

In some embodiments, cells, compositions, support compounds, and/or growth factors may be printed from separate nozzles or through the same nozzle in a common composition, depending upon the particular tissue (or tissue substitute) being formed. Printing may be simultaneous, sequential, or any combination thereof Some of the ingredients may be printed in the form of a first pattern (e.g., an erodable or degradable support material), and some of the ingredients may be printed in the form of a second pattern (e.g., cells in a pattern different from the support, or two different cell types in a different pattern). The particular combination and manner of printing will depend upon the particular tissue being printed.

The present invention includes "differentiation" and "differentiating" of cells, such as by (a) treatment of the cells to induce differentiation and completion of differentiation of the cells in response to such treatment, both prior to printing on a substrate, (b) treatment of the cells to induce differentiation, then printing of the cells on a substrate, and then differentiation of the cells in response to such treatment after they have been printed, (c) printing of the cells, simultaneously or sequentially, with a differentiation factor(s) that induces differentiation after the cells have been printed, (d) contacting the cells after printing to differentiation factors or media, etc., and combinations of all of the foregoing. In some embodiments differentiation may be modulated or delayed by contacting an appropriate factor or factors to the cell in like manner as described above. In some embodiments appropriate differentiation factors are one or more of the growth factors described above. Differentiation and modulation of differentiation can be carried out in accordance with known techniques, e.g., as described in U.S. Pat. No. 6,589,728, or U.S. Patent Application Publication Nos.: 2006006018 (endogenous repair factor production promoters); 20060013804 (modulation of stem cell differentiation by modulation of caspase-3 activity); 20050266553 (methods of regulating differentiation in stem cells); 20050227353 (methods of inducing differentiation of stem cells); 20050202428 (pluripotent stem cells); 20050153941 (cell differentiation inhibiting agent, cell culture method using the same, culture medium, and cultured cell line); 20050131212 (neural regeneration peptides and methods for their use in treatment of brain damage); 20040241856 (methods and compositions for modulating stem cells); 20040214319 (methods of regulating differentiation in stem cells); 20040161412 (cell-based VEGF delivery); 20040115810

(stem cell differentiation-inducing promoter); 20040053869 (stem cell differentiation); or variations of the above or below that will be apparent to those skilled in the art.

Support Polymers or Structural Polymers.

The support polymer or structural polymer used to create the scaffold can be any suitable material, including biodegradable or bioerodible materials, and materials that are stable or inert in vivo. Examples include, but are not limited to, poly(lactic acid) polymers, poly(glycolic acid) polymers, poly(lactide-co-glycolides) (PLGA), poly(urethanes), poly (siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(ethylene glycol), poly(methacrylic acid), polylactic acid (PLA), polyglycolic acids (PGA), nylons, polyamides, polyanhydrides, poly(ethylene-co-vinyl alcohol) (EVOH), polycaprolactone, poly(vinyl acetate), polyvinylhydroxide, poly(ethylene oxide) (PEO), and polyorthoesters or a co-polymer formed from at least two members of the group. Thus in some embodiments, the support polymer comprises, consists of or consists essentially of an aliphatic polyester. Additional examples of support polymers include, but are not limited to, natural materials with chemical modification for chemical cross-linking or photo-chemical cross-linking. e.g. gelatin, fibrinogen, gellan gum, pluronics (poloxamers), alginate, chitosan, hyaluronic acid, cellulose, and collagen. See, e.g., U.S. Pat. No. 7,531,503.

Sacrificial Polymers.

Sacrificial polymer layers and regions can be included as noted above. The sacrificial material is one which is preferably removed after fabrication. The sacrificial layer may be one which temporarily supports adjacent deposited cell-containing gel structures that would otherwise collapse during fabrication due to low mechanical strength of the gel material.

In some embodiments the sacrificial material is dispended with or alongside the cell-contained gel structure and the solidified polymer scaffold. Then, it is removed after hardening the dispensed 3D architecture (for example, after cross-linking polymers in the cell carrier composition after deposition thereof).

Any suitable material can be used for the sacrificial polymer, so long as the sacrificial polymer can be removed by techniques such as washing, warming, etc., under conditions in which the structural polymers and the cell containing compositions not substantially degraded. Examples of suitable sacrificial polymers include, but are not limited to, hydrogels (with or without chemical cross-linking) such as gelatin, fibrinogen, gellan gum, pluronics (poloxamers), alginate, chitosan, hyaluronic acid, cellulose, and collagen. Particular examples include but are not limited to compositions comprising at least one purified inverse thermosensitive polymer selected from the group consisting of poloxamers and poloxamines (e.g., poloxamer 407, poloxamer 338, poloxamer 118, poloxamine 1107 or poloxamine 1307). See, e.g., U.S. Pat. No. 7,700,086.

Sacrificial polymers are used to create openings, including pores, cavities, channels, lumens, etc. in the composite structure. The openings can be used to carry nutrients into, waste from, or active compounds into or out of, the composite. The openings can be in the form of a series of interconnecting pores interconnecting within layers, between layers, or both within and between layers. The openings can be elongate channels that branch to or from one another (e.g., as diverging branches, converging branches, or both diverging and then connected converging branches forming a capillary bed). The openings can occupy any suitable percentage of the volume of the construct (for example, from 1, 2 or 5 percent by volume, up to 50, 60, 80, 90, or 95 percent of the volume). The openings can be formed within layers, between layers, or both within and between layers, as desired.

Active or Therapeutic Agents.

In some embodiments, one or more active or therapeutic agents can be included in the cell composition, the structural or support polymer (e.g., to provide timed or delayed release thereof into adjacent cells), or both. The same or different agent can be included in different regions. Any suitable active agent (e.g., in an amount to facilitate the growth or differentiation of cells) can be used. Examples include, but are not limited to, transforming growth factor-alpha (TGF-alpha), transforming growth factor-beta (TGF-beta), platelet-derived growth factor (PDGF), fibroblast growth factor (FGF), nerve growth factor (NGF), brain derived neurotrophic factor, cartilage derived factor, bone growth factor (BGF), basic fibroblast growth factor, insulin-like growth factor (IGF), vascular endothelial growth factor (VEGF), granulocyte colony stimulating factor (G-CSF), hepatocyte growth factor, glial neurotrophic growth factor (GDNF), stem cell factor (SCF), keratinocyte growth factor (KGF), and skeletal growth factor. Stromal-derived factor (SDF), peptides such as substance P (SP), agrin, small molecules such as adenosine, etc. See, e.g., U.S. Pat. No. 7,531,503.

Systems and Apparatus.

In some embodiments, cells/compositions are printed with a modified inkjet printer. Modifications may include, but are not limited to, means to control the temperature, humidity, shear force, speed of printing, and firing frequency, by modifications of, e.g., the printer driver software and/or the physical makeup of the printer. See, e.g., Pardo et al. (2003) Langmuir 19:1462-1466; U.S. Pat. No. 7,051,654 to Boland et al. Not every modification suggested in these references will be suitable to a given application, as will be appreciated by those skilled in the art. For example, in some embodiments, printers are not modified by using new gear mount pillars with closer tolerances by adding a horizontal support, changing the transistor in the circuit to one with higher amplification, and reentering the horizontal position encoder. Also, in some embodiments, printer software is not modified to lower the resistive voltages to avoid heating of the solutions above 37 degrees C.

In some embodiments, the apparatus incorporates elements such as the syringes found in solid freeform fabrication (SFF) apparatus, particularly the syringes used for deposition of the structural support polymers.

In some embodiments, the device includes a two-dimensional (X-Y) or three-dimensional (X-Y-Z) plotter (e.g., driven by the step motors). In some embodiments, the print head is equipped with a DC solenoid inkjet valve. In some embodiments, a reservoir for loading cell print suspension is connected to the inkjet valve. In some embodiments, the cell print suspension may be supplied from the reservoirs to the inkjet valve by air pressure. In some embodiments, the print head may be mounted over an X-Y-Z plotter to allow precise deposition of cells onto a scaffold. Positioning of the XYZ plotter under the print head may be controlled via a controller. In some embodiments, the controller acquires the positioning information from software loaded on a computer. In some embodiments, the software converts the image of the target to a four-byte protocol, which is used to activate specific valves and coordinate the X-Y-Z position.

In some embodiments, the inkjet printing device (particularly for cell support compositions, or cell-containing compositions) is a thermal bubble inkjet printer. In general, in a thermal bubble inkjet printer, resistors create heat in the print head, which vaporizes ink to create a bubble. As the bubble expands, some of the ink is pushed out of a nozzle onto the paper. A vacuum is created when the bubble collapses, which pulls more ink into the print head from the cartridge. In the present invention, the ink is replaced with, e.g., cells and/or compositions of interest (e.g., cells in a liquid carrier), and the paper is replaced with a suitable substrate, e.g., an agar or collagen coated substrate, or a suitable scaffold. See, e.g., U.S. Pat. No. 6,537,567 to Niklasen et al.

In other embodiments, cells are printed using a piezoelectric crystal vibration print head. In general, a piezoelectric crystal receives an electric charge that causes it to vibrate, forcing ink out of the nozzle, and pulling more ink into the reservoir. In the present invention, the ink is replaced with, e.g., cells and/or a compositions of interest. Compared with the thermal inkjet printing, the piezo-based inkjet printing usually requires more power and higher vibration frequencies. Typical commercial piezo-printers use frequencies up to 30 kHz and power sources ranging from 12 to 100 Watts. Therefore, in some embodiments a piezoelectric crystal vibration print head is used, with a vibrating frequency of 1, 5, 10 or 15, to 20, 25, 30, or 35 or more kHz, and power sources from 5, 10, 20, 50, 100, 120, or 150, to 200, 250, 300, 350, or 375 or more Watts.

The use of an inkjet printer type syringe and nozzle for the deposition of cell-containing compositions is optional rather than mandatory herein, as cell-containing compositions can also be deposited through a solid freeform fabrication (SFF) type nozzle/syringe assembly of the type that is preferably used to deposit the structural polymer and form the three-dimensional scaffold.

In some embodiments, the system includes a computer-aided drafting and computer aided manufacturing (CAD/CAM) system to design the products to be created or convert images to a product design, control the dispensers, XYZ axis positioning, and other functions. Such CAD/CAM systems are known to those skilled in the art and can be implemented in combination with the present invention in accordance with known techniques or variations thereof that will be apparent to those skilled in the art. See, e.g., U.S. Pat. Nos. 7,472,044; 7,413,597; 7,308,386; 6,804,568; 6,775,581; 6,773,713; 6,594,539; 6,379,593; 5,930,152; and 5,757,649; the disclosures of which are incorporated by reference herein in their entirety.

Tissue and Organ Products/Implants

In some embodiments, the fabricated constructs are composed of two parts; 1) a cell-contained gel or hydrogel structure and 2) a solidified polymer or structural polymer scaffold. The polymer scaffold provides such a frame to protect the cell-contained gel structure from external loads or disruption. The system of the invention provides highly flexible design capabilities for making three-dimensional engineered constructs which contain various cells with accurate localization. Our current system has multiple syringes which can reserve both cell/gel material and synthetic polymer. Each syringe is connected with precision nozzle having micrometer scale inner diameter. And, the amount of depositing material through the nozzle can be controlled by high precision pressure control. A line structure can fabricate by scanning the nozzle connected with syringe. 2D micro pattern can fabricate by attachment of the fabricated lines. Then, a 3D structure can be fabricated by accumulating the 2D patterns in a layer-by-layer process.

A variety of organ and tissue products can be produced by the methods of the present invention, including tissues, composite tissues (two or more different tissues connected to one another at a joint or seam formed during the printing/deposition process) and organs (more than two different cells).

Examples of composite tissue constructs include, but are not limited to: Knee joint, elbow joint, wrist joint, hip joint, articulations of hand, axillary articulations, mandibular joint, sacroiliac joint, bone-articular cartilage, tendon-muscle, tendon-bone, muscle-tendon-bone, bone-ligament, bone-ligament-bone, muscle, bone, cartilage, endothelium-smooth muscle layer: blood vessels (arteries, arterioles, capillaries, venules, and veins), bladder, urethra, epithelial layer-smooth muscle layer, etc.

Examples of organs (including portions thereof) include, but are not limited to, kidney, heart, liver, pancreas, and lung.

The support polymer may be included in the construct in any suitable amount, depending on what the particular target or goal is. Thus, there is no limitation in size, volume, weight and inner/outer. Example structure size, pore size and porosity are <100 mm, 10 to 500 um and 30 to 99.9%, respectively.

"Implant" refers to a product configured to repair, augment or replace (at least a portion of) a natural tissue of a subject, e.g., for veterinary or medical (human) applications. The term "implantable" means the device can be inserted, embedded, grafted or otherwise chronically attached or placed on or in a patient. Implants include, but are not limited to, a "scaffold" or "bioscaffold" (which may or may not further comprise cells seeded onto the scaffold or bioscaffold).

"Subjects" are generally human subjects and include, but are not limited to, "patients." The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult and geriatric subjects.

Subjects may also include animal subjects, particularly vertebrate subjects, e.g., mammalian subject such as canines, felines, bovines, caprines, equines, ovines, porcines, rodents (e.g., rats and mice), lagomorphs, non-human primates, etc., or fish or avian subjects, for, e.g., veterinary medicine and/or research or laboratory purposes. "Treat" refers to any type of treatment that imparts a benefit to a subject, e.g., a patient afflicted with a trauma or a disease. For example, arthritis is a disease that affects cartilage. Treating includes actions taken and actions refrained from being taken for the purpose of improving the condition of the patient (e.g., the relief of one or more symptoms), delay in the onset or progression of the disease, etc. In some embodiments, treating includes reconstructing cartilage tissue (e.g., where such tissue has been damaged or lost by injury or disease) by implanting a scaffold into a subject in need thereof. Scaffolds may be implanted, e.g., at or adjacent to the site of injury, and/or at another site in the body of a subject that would impart a benefit to the subject, as would be appreciated by one of skill in the art.

The apparatus, methods and products of the present invention are explained in greater detail in the following non-limiting examples.

EXAMPLES

To engineer tissues, or "tissue engineered constructs" that contain multiple cell types, manual cell placement is not a feasible option. Hence, we have developed a cell delivery method and apparatus that permits accurate placement of multiple cell types, including different cell types, within a common scaffold (in the same region, in different regions, and/or in overlapping regions). In addition, we have developed a system that overcomes the limitation of using a bioprinting system that only allows the use of low viscosity biomaterials.

Our initial goal was to design a system that can process synthetic and cell mixed natural polymers with the goal of fabrication in the resolution of range of 100-200 microns. This system processes biomaterials such as polycaprolactone and gelatin.

Figure 1:
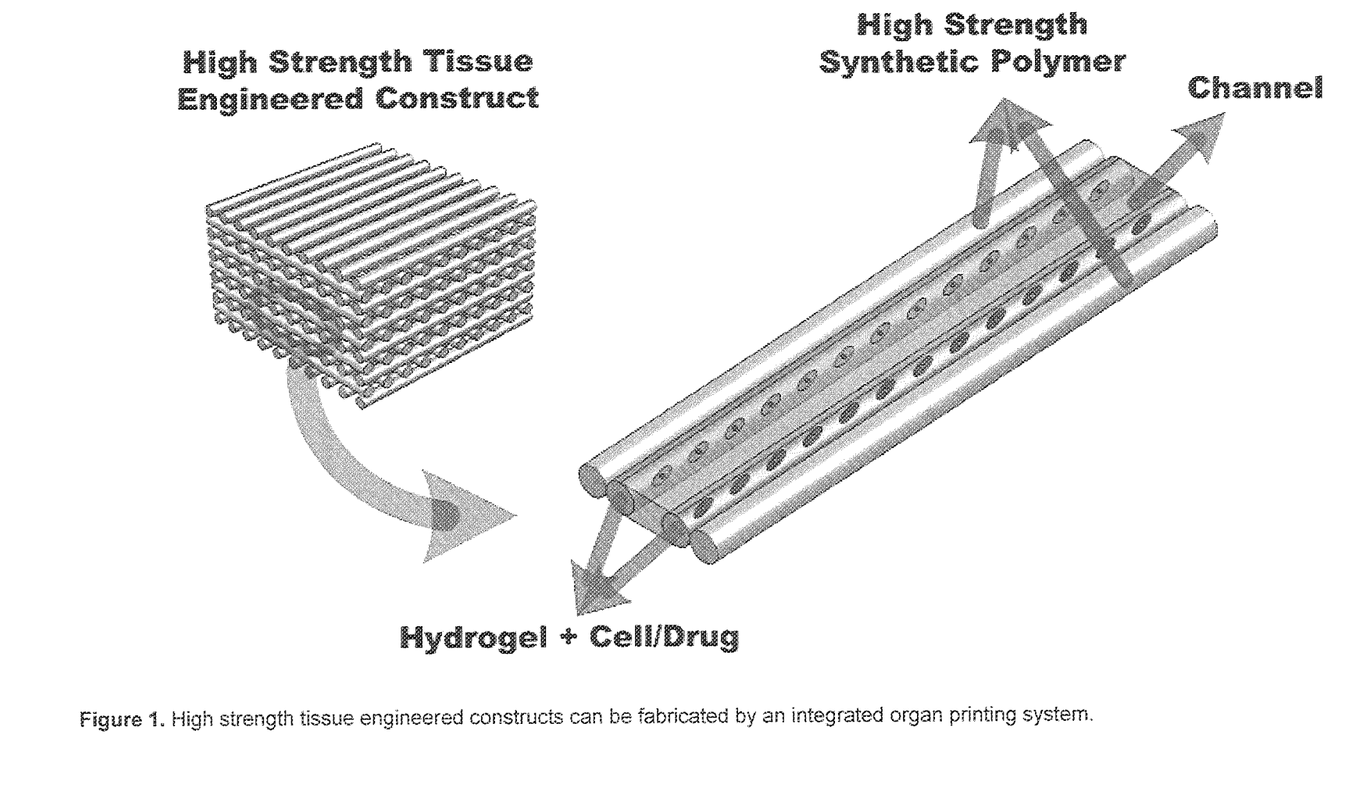
FIG. 1. Schematic illustration of one type of tissue engineered construct to be printed by systems of the method of the invention FIG. 2. Schematic illustration of an integrated printing system of the present invention useful for producing, among other things, constructs of FIG. 1.

A schematic of one embodiment of constructs or "tissue engineered constructs" produced by the present invention is shown in FIG. 1. Note that the construct is comprised of multiple layers, each layer having an axis of orientation. The axis of orientation is imparted by the orientation of the structural polymers laid down in elongate rows or columns oriented along one dimension thereof. As illustrated, the rows or columns may be generally linear and parallel, but other patterns can also be employed, and the rows or columns need not be perfectly parallel, so long as (in this non-limiting embodiment) a general axis of orientation is provided. Advantageously (in this non-limiting examples), subsequent layers (which may have a similar or dissimilar pattern) are arranged with their axis of orientation at an angle offset from that of the previous row, to enhance the structural rigidity of the construct. The degree of offset between immediately adjacent layers may be a 90 degree alternating pattern, as illustrated. However, additional degrees of offset and patterns of offset may also be used: For example: each successive layer may be offset 10, 30, 40, or 45 degrees from the previous layer (or more or less); the degree of offset between layers may vary from layer to layer; a plurality of layers may have the same orientation (whether the pattern within those layers is similar or dissimilar) followed by one or more layers with a different orientation; and combinations of all of the foregoing.

Materials and Methods.

1. Integrated Organ Printing System.

Figure 2:
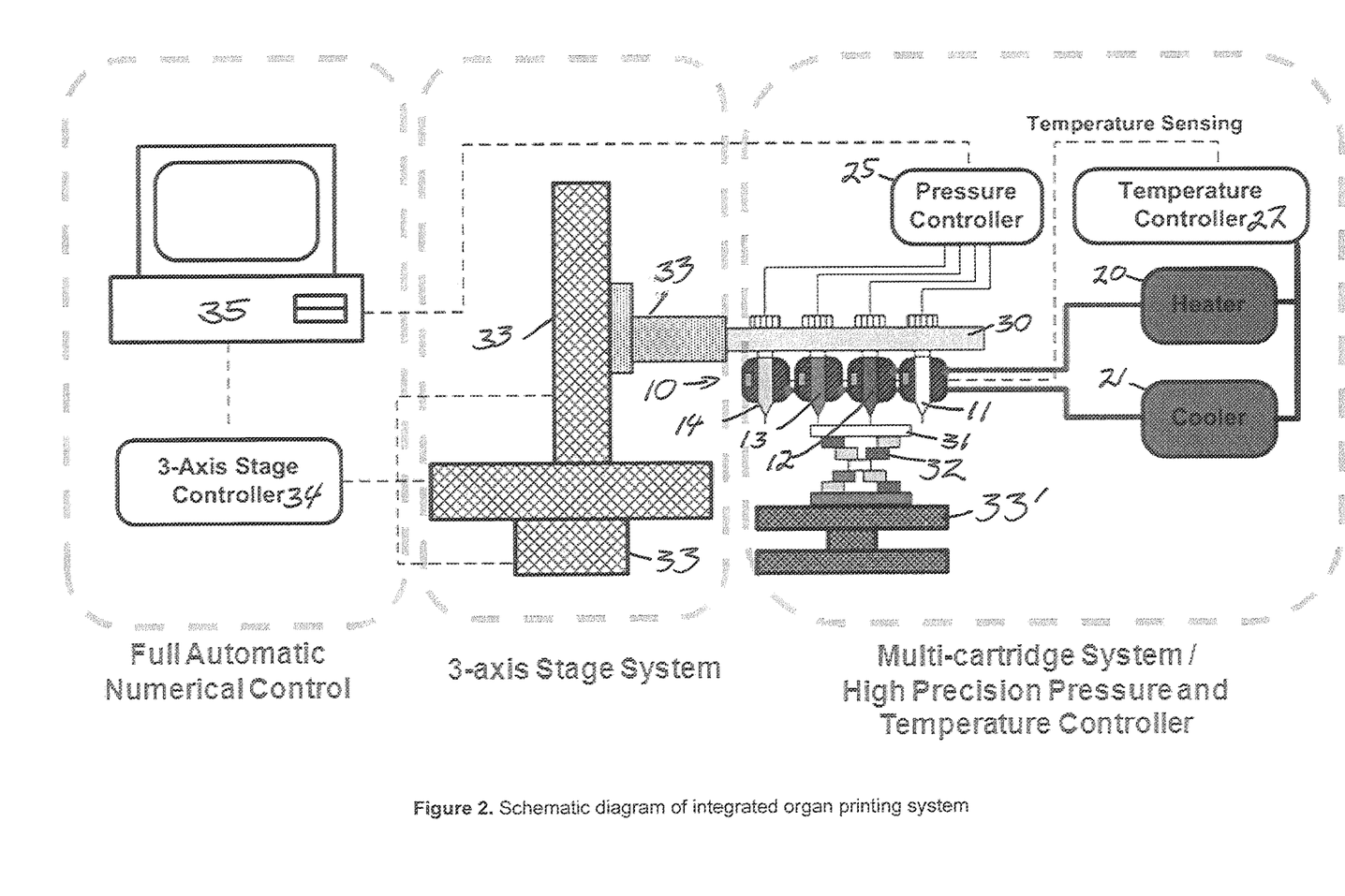

A three dimension patterning system, in this research, was constructed to realize (among other things) concurrent patterning of hydrogel mixed with cell/drug and a structural or high/higher strength synthetic polymer. FIG. 2 and shows a schematic diagram of such a system and apparatus. As shown in the figures, a multiple cartridge system 10 comprising four syringes 11, 12, 13, 14 (including syringe bodies serving as a reservoir, and syringe tips as dispensers) was adopted for concurrent patterning of various materials, with each cartridge for delivering a different material. Musashi Engineering PSY-E syringes were used. Depending upon the material being delivered, some cartridges or syringes are heated, while others are cooled, as discussed further below.

Temperature sensors, regulators (including heater 20 and cooler 21) and associated controller 22 (e.g., a Musashi Engineering TCU-02 temperature control unit for a heater; an EIC Solutions Inc. ThermoTEC™ 145 Series 1500 BTU Peltier cooler device for a cooler) are connected to and operatively associated with each syringe unit. For example, a heater is associated with one syringe unit to obtain or produce a dispensable synthetic polymer as a structural or high-strength polymer by melting (e.g., because toxic solvents are undesirable when the structural polymers are dispensed in close proximity to live cells, as is the case with the present invention); a cooler is associated with a syringe unit containing live-cell containing composition (e.g., to enhance the viability of the cells during and after deposition) or a syringe unit containing sacrificial polymer (e.g., to increase the viscosity and enhance the structural stability of the sacrificial polymer during and after deposition, up to removal thereof).

A dispenser or syringe controller such as a pressure controller 25 (e.g., a Musashi Engineering ML-808FX compact digital dispenser) is operatively associated with each syringe to provide a controller and pressure pump for each syringe.

The syringe carrier 30 and substrate 31 on substrate carrier 32 are mounted on a three 3-axis stage movement system 33, 33' with an associated controller 34 to control the positioning of the substrate and positioning of the syringes for dispensing and three dimensional patterning, respectively. For example, an Aerotech Inc. PRO165LM carrier is used to drive X and Y axis movement of the cartridge system, an Aerotech Inc. PRO115 carrier is used to drive Z axis movements of the cartridge system, an Aerotech Inc. NPAQ controller is used to control the movements of the carriers, and the NPAQ controller is programmed with Aerotech A3200-MC software. All can in turn be controlled by CAD/CAM software programmed in a suitable computer 35 in MICROSOFT C++ Visual on a DELL desktop computer. In the Figures, electrical and pneumatic lines are shown in part and omitted in part for clarity.

2. Cell Cultures.

NIH3T3 mouse fibroblast cells were cultured on a 150 cm culture dish. High glucose DMEM with 10% FBS, 1% penicillin and 1% antibiotics were used as culture medium. The medium was exchanged every 2 to 3 days. And, subculture were conducted on about 70 to 80% confluence with 0.05% Tripsin.

3. Cell Carrier Material Preparation.

In this example four separate components, including gelatin, fibrinogen, glycerol, and hyaluronic acid, were combined to serve as a cell carrier material. Before cell patterning, various mixtures having different compositions as listed in Table 1 below were tested to investigate dispensing performances. And, one of these compositions was used for two dimensional and three dimensional cell patterning.

The cells were carefully mixed with the material at 37° C. because the material is a viscous fluid. The cell concentration was $10^6$ cells/ml in the mixture. Then, the mixture was immediately transferred into an ice bath to induce fast gel formation of gelatin. This hydrogel was used for further cell patterning experiments.

4. Cell Patterning

A. Two dimensional patterning test. Various mixtures were tested to investigate their dispensing performance. The dispensing volume was observed with a microscope. Then, its stability was scored by comparing each material. One of these materials (gelatin 20 mg/ml, hyaluronic acid 3 mg/ml, fibrinogen 10 mg/ml, and glycerol 10% v/v), was selected as a cell carrier material for further study.

Cells were labeled with fluorescent dye (Vybrant Multicolor Cell-labeling Kit, Invitrogen Inc.) before mixing with the cell carrier material. The cell mixture was prepared as described above. The mixture was loaded into the printing system. For this particular test a 120 μm nozzle, 90 KPa air pressure and 250 mm/min scanning speed were used for the two-dimensional cell patterning test.

B. Three-dimensional cell patterning of a tissue engineered construct. The material used in two dimensional patterning experiment described above was used in this three dimensional patterning experiment. In addition, poly(ε- caprolactone) (PCL, Polysciences Inc., mw: 43,000~50,000) were used as a structural support polymer (sometimes also referred to as a "high strength material.") The three dimensional hybrid structure was hence composed of high strength synthetic polymer, and a cell loaded hydrogel, fabricated by concurrent patterning of the two different materials.

Figure 3:
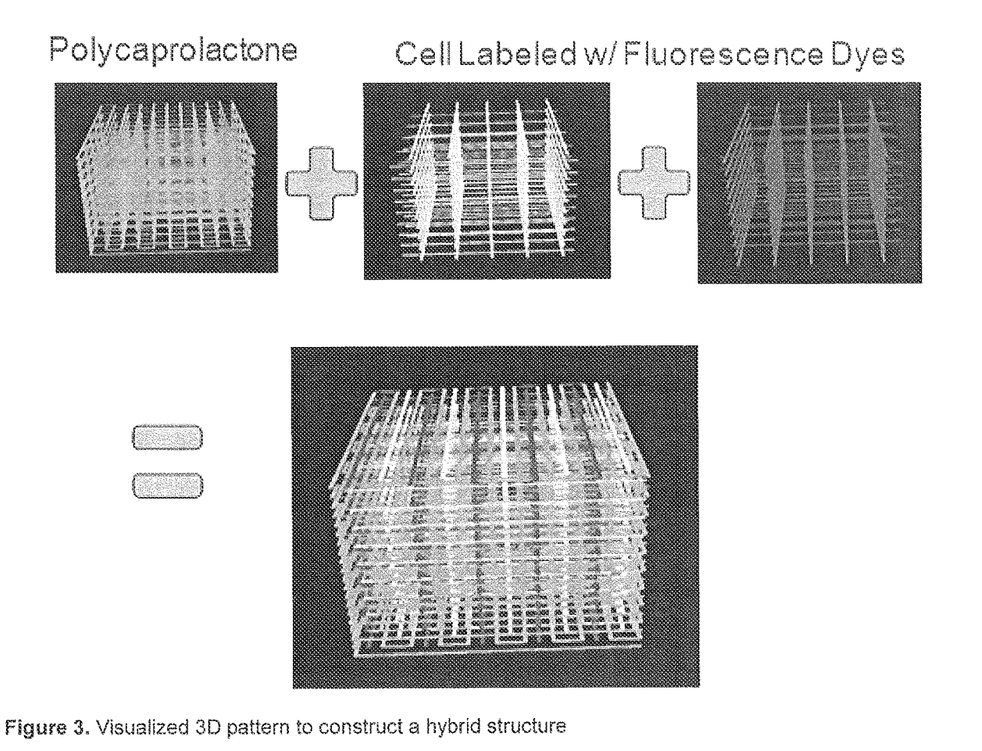
FIG. 3. A visualized 3D pattern for a hybrid structure to be produced by a system and method of the present invention.

FIG. 3 shows a visualized three-dimensional pattern for use in fabricating a hybrid structure. As shown in the figure, three different materials: PCL as a structural polymer; cells labeled with a first fluorescent dye, and cells labeled with a second fluorescent dye, were concurrently deposited as a pattern to produce a single composite structure. After fabricating the composite structure, thrombin solution (10 units/ml in 40 mM $CaCl_2$)) was added into the structure to induce crosslinking of the fibrinogen (stabilizing the cell-containing material). After one hour, the construct it was carefully washed with phosphate-buffered saline (PBS) and cell culture medium was added. To confirm the cell positioning in the construct, cyro-sectioning was conducted with the fabricated structure and sections imaged by fluorescence microscopy.

C. Cell viability test. Cell viability tests were conducted to evaluate cell compatibility with the patterning system, process, and construct. Live/dead viability/cytotoxicity kits (Invitrogen Inc.) and the Alamar Blue assay were used. The protocols recommended by the manufacturer were used for evaluation. The fabricated construct was stained with the live/dead viability/cytotoxicity kit. Then, fluorescent images were obtained to distinguish live and dead cells. The number of live and total cells in an image was manually counted. Then, cell viability was calculated as percentage of the number of live cells in the image. Cell proliferation was investigated by the Alamar Blue assay for 5 days.

Results.

1. Dispensing Stability Test of Various Material Compositions

Figure 4:
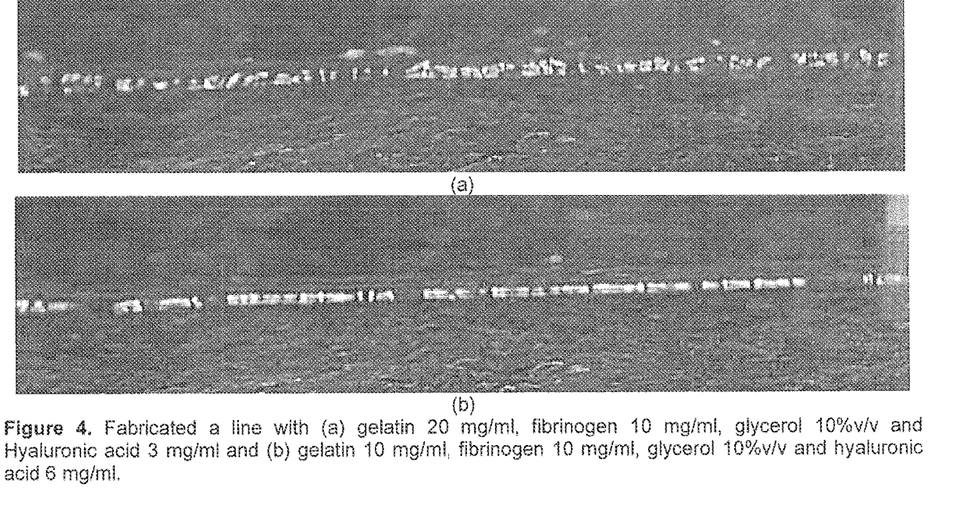
FIG. 4. Fabricated of a line with: (a) gelatin 20 mg/ml, fibrinogen 10 mg/ml, glycerol 10% v/v and Hyaluronic acid 3 mg/ml, and with (b) gelatin 10 mg/ml, fibrinogen 10 mg/ml, glycerol 10% v/v and hyaluronic acid 6 mg/ml.

FIG. 4 shows dispensing results for two different materials. Higher gelatin means higher instability of dispensing volume. The results were scored as listed in the Table 1.

2. Two Dimensional Cell Patterning

Figure 5:
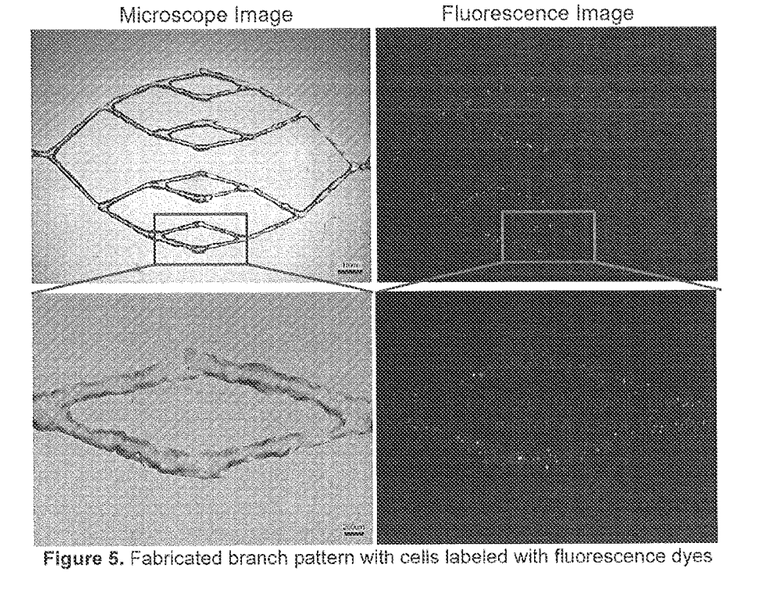
FIG. 5. Fabrication of a branch pattern (specifically, diverging, and then converging, branches, in a form like that of a capillary bed) with a composition containing cells labeled with fluorescent dyes.

FIG. 5 shows patterning results with cells labeled with fluorescent dyes. Left side was patterned with cells labeled with green color and right side was red color. An approximately 100 um wide line was obtained with the system. And, cells were labeled with two different colors were successfully patterned as a single structure. Note that diverging and converging branch patterns were produced, analogous to a "capillary bed" (And, while widths of columns are held constant, note also that they may be varied as desired).

TABLE 1

Material compositions for cell carrier materials and dispensing stability

| Material Composition | | | | |
|---|---|---|---|---|
| Gelatin (mg/ml) | Hyaluronic Acid(mg/ml) | Fibrinogen (mg/ml) | Glycerol (% v/v) | Dispensing Stability |
| 20 | 3.0 | 10.0 | 10 | − |
| 20 | 3.0 | 10.0 | 15 | Unmixed |
| 15 | 3.0 | 10.0 | 15 | Unmixed |
| 17.5 | 3.0 | 10.0 | 10 | − |
| 15 | 3.0 | 10.0 | 10 | + |
| 10 | 3.0 | 10.0 | 10 | ++ |
| 10 | 6.0 | 10.0 | 10 | ++ |

Figure 6:
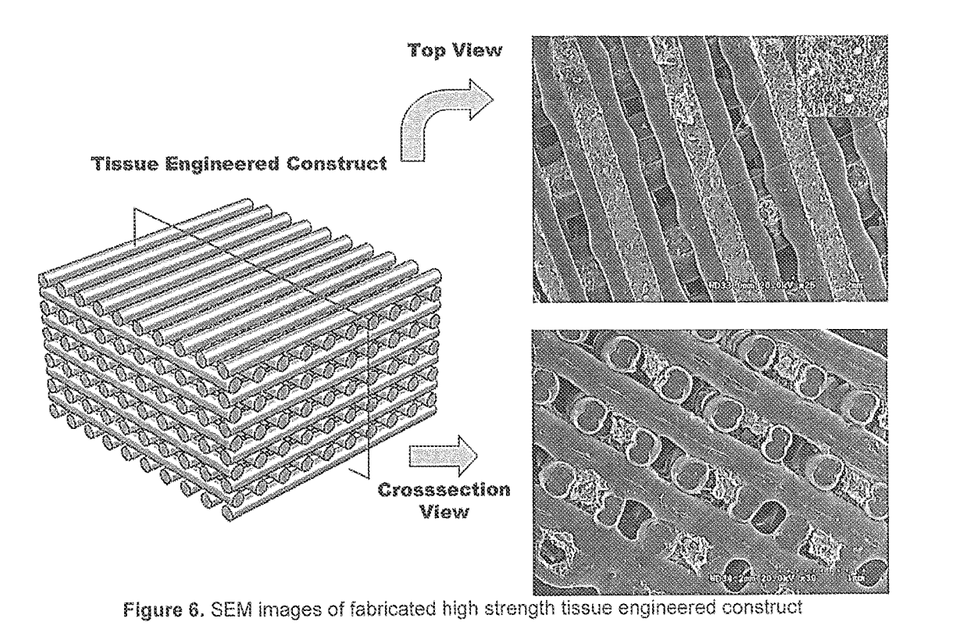
FIG. 6. SEM images of fabricated high strength tissue engineered construct.
Figure 7:
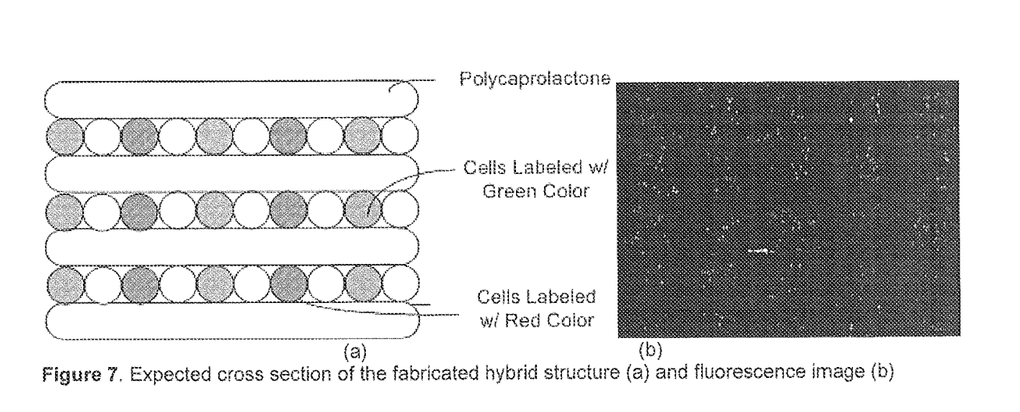
FIG. 7. Expected cross section of the fabricated hybrid structure (a) and fluorescence image.

3. Three Dimensional Cell Patterning in the High Strength Tissue Engineered Construct FIG. 6 and FIG. 7 show the fabricated high strength tissue engineered construct and fluorescence image of its cyro-sectioned sample. A three dimensional structure as planned (see FIG. 4) was achieved in the product shown, with cells were successfully placed into the desired position.

4. Cell Viability

Figure 8:
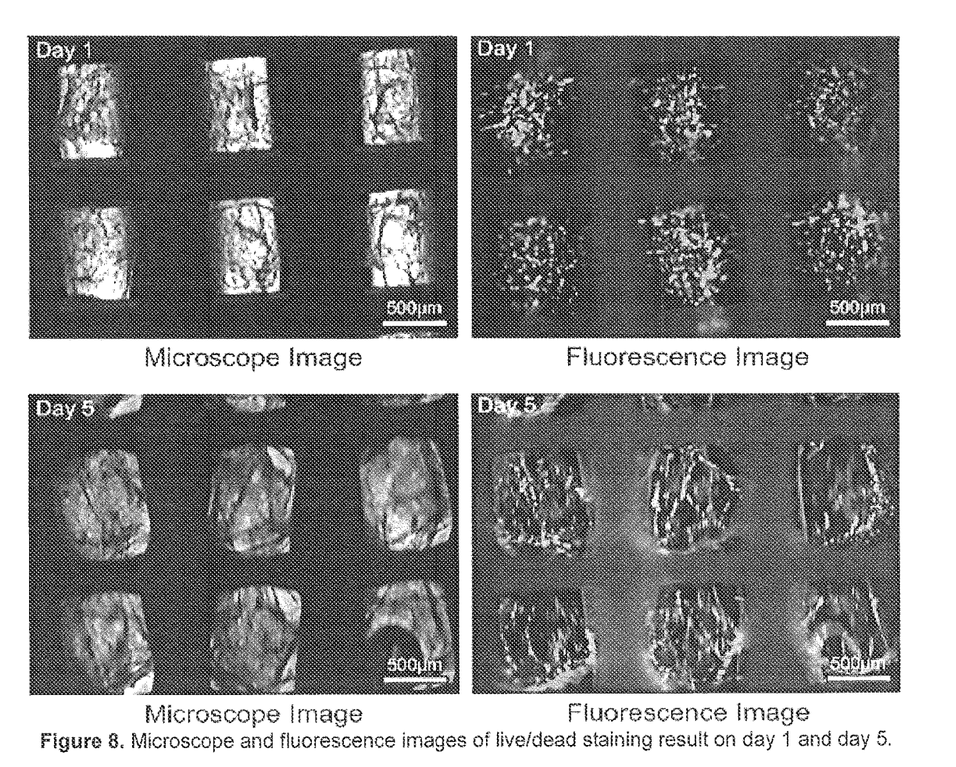
FIG. 8. Microscope and fluorescence images of live/dead staining results on day 1 and day 5 after production of a tissue engineered construct of the present invention.

FIG. 8 shows light microscope and fluorescent microscopy images of live/dead assay on 1 and 5 days. Although not easily seen in the black-and-white Figure, live cells show in a green color and dead cell show in a red color. The cells in the showed their morphology on day 1, and started proliferation.

Figure 9:
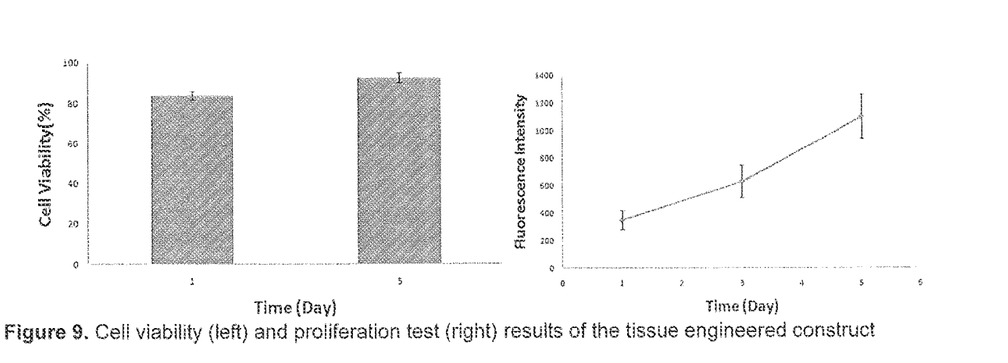
FIG. 9. Cell viability (left) and cell proliferation (right) test results for a tissue engineered construct of the present invention.

FIG. 9 shows the calculated cell viability and Alamar Blue assay results. About 83% cell viability was seen on 1 day. Then, the viability increased on day 5 as a result of cell proliferation. This trend also can be observed on the proliferation test result. These data demonstrate the practicability of a method and apparatus of the invention.

REFERENCES

The following references are incorporated herein by reference in their entirety.

1. Boland et al., Ink-jet printing of viable cells, U.S. Pat. No. 7,051,654.
2. Warren et al., Architecture tool and methods of use, U.S. Pat. No. 6,986,739.
3. Omotunde Babalola et al., Biological scaffold, US Patent Application Publication No. 2006/0094112.
4. Vacanti et al., Vascularized tissue regneration matrices formed by solid freeform fabrication techniques, U.S. Pat. No. 6,176,874.
5. Vacanti et al., Fabrication of vascularized tissue, U.S. Pat. No. 6,455,31.
6. Linda G. Cima et al., Preparation of medical devices by solid free-form fabrication methods, U.S. Pat. No. 5,490,962.
7. Linda G. Cima et al., Tissue regeneration matrices by solid free form fabrication techniques, U.S. Pat. No. 5,518,680.
8. Phil G. Campbell et al., Method and apparatus for preparing biomimetic scaffold, US Patent Publication No. US 2003/0175410.

The foregoing is illustrative of the present invention, and is not to be construed as limiting thereof. The invention is defined by the following claims, with equivalents of the claims to be included therein.

The invention claimed is:

1. A three-dimensional tissue or organ construct comprising:
   a three-dimensional scaffold of a structural support polymer in combination with a live cell-containing composition,
   wherein said tissue or organ construct comprises a layer with separate and discrete regions therein, and first regions of the separate and discrete regions comprise said structural support polymer, and second regions of the separate and discrete regions comprise said live cell-containing composition.

2. The three-dimensional tissue or organ construct of claim 1, wherein said construct further comprises openings formed therein.

3. The three-dimensional tissue or organ construct of claim 2, wherein said openings comprise pores, cavities, chambers, vessel lumens or channels formed therein.

4. The three-dimensional tissue or organ construct of claim 1, wherein said construct further comprises openings therein, and said scaffold comprises a plurality of layers, and said openings are formed within said layers, between said layers, or both within and between said layers.

5. The three-dimensional tissue or organ construct of claim 1, wherein said live cell-containing composition comprises a hydrogel.

6. The three-dimensional tissue or organ construct of claim 1, wherein said tissue or organ construct comprises two or more different tissues, said two or more different tissues sharing a common, integrally formed and connected, solid support scaffold.

7. The three-dimensional tissue or organ construct of claim 1, wherein the layer is one of a plurality of layers of said tissue or organ construct, first layers of said layers having a first axis of orientation, and second layers of said layers having a second axis of orientation sufficiently different from the first axis of orientation to enhance the structural rigidity of said scaffold.

8. The three-dimensional tissue or organ construct of claim 1, wherein the layer is one of a plurality of layers of said tissue or organ construct, and
the first regions of the separate and discrete regions of adjacent layers of the plurality of layers overlap with one another.

9. The three-dimensional tissue or organ construct of claim 1, wherein a cell concentration of said cell-containing composition is about $10^6$ cells/ml.

10. The three-dimensional tissue or organ construct of claim 1, wherein said cell-containing composition comprises gelatin, hyaluronic acid and fibrinogen.

* * * * *